(12) United States Patent
Mantelle

(10) Patent No.: US 9,320,742 B2
(45) Date of Patent: Apr. 26, 2016

(54) TRANSDERMAL TESTOSTERONE DEVICE AND DELIVERY

(75) Inventor: Juan A. Mantelle, Miami, FL (US)

(73) Assignee: NOVEN PHARMACEUTICALS, INC., Miami, FL (US)

( * ) Notice: Subject to any disclaimer, the term of this patent is extended or adjusted under 35 U.S.C. 154(b) by 477 days.

(21) Appl. No.: 12/953,019

(22) Filed: Nov. 23, 2010

(65) Prior Publication Data

US 2011/0129535 A1 Jun. 2, 2011

Related U.S. Application Data

(60) Provisional application No. 61/265,411, filed on Dec. 1, 2009.

(51) Int. Cl.
| | | |
|---|---|---|
| *A61K 9/00* | (2006.01) | |
| *A61K 31/568* | (2006.01) | |
| *A61K 9/70* | (2006.01) | |
| *A61P 15/00* | (2006.01) | |
| *A61P 5/26* | (2006.01) | |
| *A61P 9/00* | (2006.01) | |

(52) U.S. Cl.
CPC .............. *A61K 31/568* (2013.01); *A61K 9/7061* (2013.01); *A61K 9/7069* (2013.01)

(58) Field of Classification Search
CPC .. A61K 9/7061; A61K 9/7069; A61K 31/568
See application file for complete search history.

(56) References Cited

U.S. PATENT DOCUMENTS

| | | |
|---|---|---|
| 5,234,957 A | 8/1993 | Mantelle |
| 5,300,291 A | 4/1994 | Mantelle et al. |
| 5,332,576 A | 7/1994 | Mantelle |
| 5,446,070 A | 8/1995 | Mantelle |
| 5,460,820 A | 10/1995 | Ebert et al. |
| 5,474,783 A | 12/1995 | Miranda et al. |
| 5,656,286 A | 8/1997 | Miranda et al. |
| 5,719,197 A | 2/1998 | Mantelle |
| 5,958,446 A | 9/1999 | Miranda et al. |
| 6,024,976 A | 2/2000 | Miranda et al. |
| 6,221,383 B1 | 4/2001 | Miranda et al. |
| 6,231,885 B1 * | 5/2001 | Carrara .......................... 424/448 |
| 6,235,306 B1 | 5/2001 | Miranda et al. |
| 6,316,022 B1 | 11/2001 | Mantelle et al. |
| 7,456,159 B2 | 11/2008 | Houze et al. |
| 7,846,916 B2 | 12/2010 | Houze et al. |
| 7,867,986 B2 | 1/2011 | Houze et al. |
| 7,879,831 B2 | 2/2011 | Houze et al. |
| 7,993,671 B2 | 8/2011 | Mantelle et al. |
| 8,025,898 B2 | 9/2011 | Houze et al. |
| 8,110,565 B2 | 2/2012 | Houze et al. |
| 8,187,628 B2 | 5/2012 | Houze et al. |
| 8,216,606 B2 | 7/2012 | Houze et al. |
| 2006/0078601 A1 | 4/2006 | Kanios et al. |
| 2006/0078602 A1 | 4/2006 | Kanios et al. |

FOREIGN PATENT DOCUMENTS

WO   WO 2009/142699 A1   11/2009

OTHER PUBLICATIONS

U.S. Appl. No. 13/229,007, filed Sep. 9, 2011, Kanios et al.
Williams & Wilkins, "Drugs for Female Sexual Dysfunction," Obstetrics and Gynecology, vol. 110, No. 4, pp. 918-919, Oct. 1, 2007.
Seftel, "Testosterone replacement therapy for male hypogonadism: Part III. Pharmacologic and clinical profiles, monitoring, safety issues and potential future agents," International Journal of Impotence Research, vol. 19, No. 1, pp. 2-24, Jan. 1, 2007.
International Search Report issued in application No. PCT/US2010/057797 on Apr. 13, 2011.

* cited by examiner

*Primary Examiner* — Suzanne Ziska
*Assistant Examiner* — Thurman Wheeler
(74) *Attorney, Agent, or Firm* — Foley & Lardner LLP

(57) ABSTRACT

Described are transdermal drug delivery systems for the transdermal administration of testosterone, comprising a polymer matrix and testosterone. Methods of making and using such systems also are described.

11 Claims, 1 Drawing Sheet

TRANSDERMAL TESTOSTERONE DEVICE AND DELIVERY

CROSS-REFERENCE TO RELATED APPLICATIONS

This application claims priority to U.S. 61/265,411, filed Dec. 1, 2009, the entire contents of which are incorporated herein by reference.

FIELD OF THE INVENTION

Described herein are compositions and methods for the transdermal delivery of testosterone.

BACKGROUND

This invention relates generally to transdermal drug delivery systems, and more particularly, to transdermal drug delivery systems for the delivery of testosterone. The use of a transdermal system, for example, a patch comprising a pressure-sensitive adhesive containing a drug, as a means of delivering drug through the skin is well known. However, there remains a need for transdermal drug delivery systems designed for the delivery of specific drugs, such as testosterone, and there remains a particular need for smaller transdermal drug delivery systems that exhibit desired pharmacokinetic properties.

Transdermal delivery systems (adhesive patches) as dosage forms have been the subject of a vast number of patent applications over the last 25 years, yielding many patents but few commercial products in comparison. To those working in the field, the relatively small number of commercial products is not surprising. Although regulatory, economic, and market hurdles play a role in limiting the number of products on the market, the task of developing a transdermal delivery system that achieves desired physical and pharmacokinetic parameters to satisfy physician and patient demand is more daunting. Parameters to be considered during commercial product development may include drug solubility, drug stability (e.g., as may arise from interaction with other component materials and/or the environment), delivery of a therapeutic amount of drug at a desired delivery rate over the intended duration of use, adequate adhesion at the anatomical site of application, integrity (e.g., minimal curling, wrinkling, delaminating and slippage) with minimal discomfort, irritation and sensitization both during use and during and after removal, and minimal residual adhesive (or other components) after removal. Size also may be important from a manufacturing and patient viewpoint, and appearance may be important from a patient viewpoint. The physical manufacturing and production aspects of commercial product development (e.g., the identity and costs of materials, equipment, and labor) and supporting analytical methods required for regulatory compliance also can be significant.

Of the physical parameters that are considered when developing a commercial transdermal drug delivery system, size, e.g., surface area at the site of application, is often dictated and limited by other physical and pharmacokinetic requirements, such as desired drug delivery rates and daily dosages. In general, it is easier to develop a relatively "large" transdermal drug delivery system that will achieve drug delivery at target therapeutic levels over an intended duration of therapy, than it is to develop a smaller transdermal drug delivery system that still exhibits acceptable pharmacokinetic properties. Still, because size directly impacts costs (e.g., costs of component materials, costs of packaging materials, costs for production and manufacturing equipment, labor costs relative to product yield per run time, etc.) and patients generally prefer smaller systems to larger ones (both for aesthetic reasons and comfort, since a smaller surface may permit the use of less aggressive adhesives), there is a need for smaller transdermal drug delivery systems.

SUMMARY

In accordance with one embodiment, there is provided a transdermal drug delivery system comprising a drug containing layer defining an active surface area and comprising a polymer matrix comprising testosterone, wherein the system includes less than 0.3 mg/cm$^2$ testosterone and achieves a testosterone flux that is at least about 0.7 µg/cm$^2$/hour, such as at least about 0.89 µg/cm$^2$/hour, based on the active surface area. In some embodiments, the polymer matrix comprises a polymer blend comprising an acrylic adhesive, a silicone adhesive, and soluble PVP. In some embodiments, the polymer matrix comprises about 2-25% by weight acrylic adhesive, about 45-70% by weight silicone adhesive, about 2-25% by weight soluble PVP, about 0-15% penetration enhancer, about 0.1-10% by weight testosterone, and, optionally, about 0.001-0.1% by weight antioxidant, all based on the total dry weight of the polymer matrix. In some embodiments, the polymer matrix comprises about 20% by weight acrylic adhesive, about 59% by weight silicone adhesive, about 12% by weight soluble PVP, about 6.0% by weight oleyl alcohol, about 2-3% by weight testosterone, and, optionally about 0.01% by weight butylhydroxytoluene, all based on the total dry weight of the polymer matrix. In some embodiments, the acrylic adhesive and silicone adhesive are present in a ratio of from about 1:2 to about 1:6, based on the total weight of the acrylic and silicone adhesives.

In some embodiments, the penetration enhancer comprises oleyl alcohol or dipropylene glycol, or both.

In some embodiments, the polymer matrix comprises an amount of testosterone effective to deliver a therapeutically effective amount of testosterone over a period of time selected from the group consisting of at least 1 day, at least 2 days, at least 3 days, at least 4 days, at least 5 days, at least 6 days and at least 7 days. In some embodiments, the polymer matrix comprises an amount of testosterone effective to deliver an amount of testosterone of at least 300 µg/day, over a period of at least 3 days.

In some embodiments, the polymer matrix has a coat weight of greater than about 10 mg/cm$^2$. In some embodiments, the polymer matrix has a coat weight selected from the group consisting of about 12.0, about 12.5, about 13.0 and about 15 mg/cm$^2$.

In accordance with some embodiments, there is provided a transdermal drug delivery system comprising a polymer matrix comprising testosterone, wherein the system has an active surface area that is about 50% of 28.0 cm$^2$, including about 14 cm$^2$, and is effective to deliver an amount of testosterone per day of at least 300 µg/day.

In accordance with some embodiments, there is provided a method for administering testosterone, comprising applying to the skin or mucosa of a subject in need thereof a transdermal drug delivery system comprising a drug-containing layer defining an active surface area and comprising a polymer matrix comprising testosterone, wherein the system includes less than 0.3 mg/cm$^2$ testosterone and achieves an testosterone flux that is at least about 0.7 µg/cm$^2$/hour, such as at least about 0.89 µg/cm$^2$/hour, based on the active surface area. In some embodiments, the system has an active surface area that is about 50% of 28.0 cm², including about 14 cm², and is effective to deliver an amount of testosterone per day of at least 300 µg/day.

In accordance with some embodiments, there is provided a method of making a transdermal drug delivery system for administering testosterone, comprising forming a polymer matrix comprising testosterone and a polymer blend comprising an acrylic adhesive, a silicone adhesive, and soluble PVP, and applying the polymer matrix to a support layer such that the system includes less than 0.3 mg/cm² testosterone. In some embodiments, the system has an active surface area that is about 50% of 28.0 cm², including about 14 cm². In some embodiments, the polymer matrix comprises about 20% by weight acrylic adhesive, about 59% by weight silicone adhesive, about 12% by weight soluble PVP, about 6.0% by weight oleyl alcohol, about 2-3% by weight testosterone and, optionally about 0.01% by weight butylhydroxytoluene, all based on the total dry weight of the polymer matrix. In some embodiments, the polymer matrix is applied to the support layer at a coat weight of greater than about 10 mg/cm². In some embodiments, the polymer matrix coat weight is selected from the group consisting of 12.0, about 12.5, about 13.0 and about 15 mg/cm².

DETAILED DESCRIPTION

Figure 1:
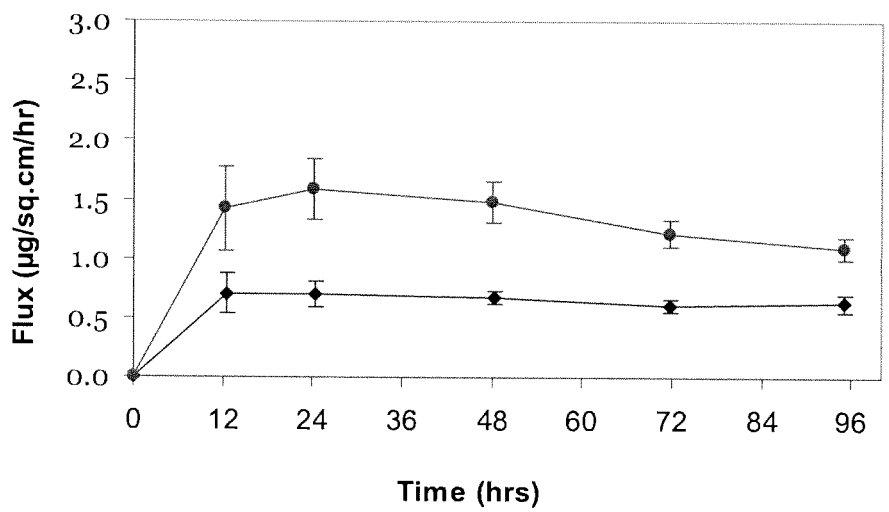
FIG. 1 illustrates the testosterone flux (µg/cm²/hr) over time (0-96 hours) from a transdermal delivery system according to the invention (●), as compared to Intrinsa® (♦).

The field of transdermal delivery systems suffers from the problem of needing to balance many different competing factors to develop a commercial product that exhibits, for example both clinical efficacy and satisfactory wear properties while remaining acceptable to patients. For example, when selecting the size of a transdermal delivery system, it is necessary to balance factors that favor a smaller size (such as lower cost, better adhesive performance and improved aesthetics) against factors that favor a larger size (such as the target delivery rate (flux) and daily dose). The Intrinsa® transdermal testosterone product (manufactured by Watson Pharmaceuticals Inc.) is 28 cm² and contains 8.4 mg of testosterone. Thus, the Intrinsa® product includes 0.3 mg/cm² testosterone. The Intrinsa® product is said to deliver 300 µg testosterone per day.

In accordance with some embodiments, the present invention provides transdermal drug delivery systems for the transdermal delivery of testosterone that have a smaller active surface area than Intrinsa® but achieve daily dosages that are about equal to or greater than the Intrinsa® products. For example, the present invention includes transdermal drug delivery systems that achieve daily dosages that are about equal to an Intrinsa® product, in a smaller sized system. The ability to provide a smaller system without sacrificing daily dosage represents a significant advance.

Applicant surprisingly discovered that adjusting the coat weight of the drug-containing adhesive layer could be used to adjust the flux per unit area, and thus permitted the development of smaller transdermal drug delivery systems that achieve comparable daily dosages. This result is surprising because coat weight is typically selected to control the duration of delivery, but is not generally understood to impact delivery rate. Thus, while it is known in the art to increase coat weight to provide delivery over a longer period of time, it was not known that increasing coat weight could increase delivery rate or flux, and thus permit the development of a smaller system while maintaining daily dosage.

Moreover, Applicant surprisingly discovered that the drug-containing adhesive layers described herein achieve a flux per unit area that is greater than that of the Intrinsa® product, but with a similar amount drug per unit area. This permitted the development of smaller transdermal drug delivery systems that achieve comparable daily dosages. This result is surprising because Applicant is able to achieve comparable drug delivery with less drug.

In accordance with some aspects, there are provided transdermal drug delivery systems and methods for the transdermal delivery of testosterone. In specific embodiments, the systems exhibit increased flux than other known testosterone devices (such as Intrinsa®, manufactured by Watson Pharmaceuticals Inc.) and, therefore, exhibit increased drug delivery per unit area. For example, in some embodiments, the systems exhibit a flux greater than the about 0.45 µg/cm²/hour exhibited by the Intrinsa® product, such as a flux that is at least about 0.70 µg/cm²/hour, including a flux that is at least 0.70 µg/cm²/hour, including a flux that is at least about 0.89 µg/cm²/hour, at least 0.89 µg/cm²/hour, at least about 1.0 µg/cm²/hour, at least 1.0 µg/cm²/hour, at least about 1.5 µg/cm²/hour, and at least 1.5 µg/cm²/hour. In some embodiments, the systems described herein achieve a flux that at least is about 0.70 µg/cm²/hour, including at least 0.70 µg/cm²/hour, at least about 0.89 µg/cm²/hour, at least 0.89 µg/cm²/hour, at least about 1.0 µg/cm²/hour, at least 1.0 µg/cm²/hour, at least about 1.5 µg/cm²/hour, or at least 1.5 µg/cm²/hour, over a period of time of a least 3 days, including a period of time of 3 days, or a period of time of 4 days or longer.

In some embodiments, the systems have a lower amount of drug per unit area than other known testosterone devices, but still achieve effective drug delivery. For example, in some embodiments, the systems have a coat weight such that the amount of testosterone per unit area is less than the 0.3 mg/cm² testosterone of the Intrinsa® product, such as an amount of drug per unit area of about 0.28 mg/cm².

Thus, in accordance with some aspects, the invention permits the use of smaller devices to achieve comparable drug delivery.

DEFINITIONS

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Any suitable materials and/or methods known to those of ordinary skill in the art can be utilized in carrying out the present invention. However, specific materials and methods are described. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The phrase "substantially free" as used herein generally means that the described composition (e.g., transdermal drug delivery system, polymer matrix, etc.) comprises less than about 5%, less than about 3%, or less than about 1% by weight, based on the total weight of the composition at issue, of the excluded component.

As used herein "subject" denotes any animal in need of drug therapy, including humans. For example, a subject may be suffering from or at risk of developing a condition that can be treated or prevented with testosterone, or may be taking testosterone for health maintenance purposes.

As used herein, the phrases "therapeutically effective amount" and "therapeutic level" mean that drug dosage or plasma concentration in a subject, respectively, that provides the specific pharmacological response for which the drug is administered in a subject in need of such treatment. It is emphasized that a therapeutically effective amount or therapeutic level of a drug will not always be effective in treating the conditions/diseases described herein, even though such dosage is deemed to be a therapeutically effective amount by those of skill in the art. For convenience only, exemplary dosages, drug delivery amounts, therapeutically effective amounts and therapeutic levels are provided below with reference to adult human subjects. Those skilled in the art can adjust such amounts in accordance with standard practices as needed to treat a specific subject and/or condition/disease.

As used herein, "active surface area" means the surface area of the drug-containing layer of the transdermal drug delivery system.

As used herein, "coat weight" refers to the weight of the drug-containing layer per unit area of the active surface area of the transdermal drug delivery system.

As used herein, "testosterone" includes androgenic steroids such as testosterone, testosterone acetate, testosterone enanthate, testosterone proprionate, 17-beta-cypionate, testosterone nicotinate, testosterone phenylacetate, and non-esters that have groups on the 17 position, such as testosterone 17-chloral hemiacetal.

As used herein, "flux" (also called "permeation rate") is defined as the absorption of a drug through skin or mucosal tissue, and is described by Fick's first law of diffusion:

$$J = -D(dCm/dx)$$

where J is the flux in $g/cm^2/sec$, D is the diffusion coefficient of the drug through the skin or mucosa in $cm^2/sec$ and $dCm/dx$ is the concentration gradient of the drug across the skin or mucosa.

As used herein, the term "transdermal" refers to delivery, administration or application of a drug by means of direct contact with skin or mucosa. Such delivery, administration or application is also known as dermal, percutaneous, transmucosal and buccal. As used herein, "dermal" includes skin and mucosa, which includes oral, buccal, nasal, rectal and vaginal mucosa.

As used herein, "transdermal drug delivery system" refers to a system (e.g., a device) comprising a composition that releases testosterone upon application to the skin (or any other surface noted above). A transdermal drug delivery system may comprise a drug-containing layer, and, optionally, a backing layer and/or a release liner layer. In some embodiments, the transdermal drug delivery system is a substantially non-aqueous, solid form, capable of conforming to the surface with which it comes into contact, and capable of maintaining such contact so as to facilitate topical application without adverse physiological response, and without being appreciably decomposed by aqueous contact during topical application to a subject. Many such systems are known in the art and commercially available, such as transdermal drug delivery patches. As described below, in one embodiment, the transdermal drug delivery system comprises a drug-containing polymer matrix that comprises a pressure-sensitive adhesive or bioadhesive, and is adopted for direct application to a user's (e.g., a subject's) skin. In other embodiments, the polymer matrix is non-adhesive and may be provided with separate adhesion means (such as a separate adhesive layer) for application and adherence to the user's skin.

As used herein, "polymer matrix" refers to a polymer composition which contains one or more drugs. In some embodiments, the matrix comprises a pressure-sensitive adhesive polymer or a bioadhesive polymer. In other embodiments, the matrix does not comprise a pressure-sensitive adhesive or bioadhesive. As used herein, a polymer is an "adhesive" if it has the properties of an adhesive per se, or if it functions as an adhesive by the addition of tackifiers, plasticizers, crosslinking agents or other additives. Thus, in some embodiments, the polymer matrix comprises a pressure-sensitive adhesive polymer or a bioadhesive polymer, with testosterone dissolved or dispersed therein. The polymer matrix also may comprise tackifiers, plasticizers, crosslinking agents, enhancers, co-solvents, fillers, antioxidants, solubilizers, crystallization inhibitors, or other additives described herein. U.S. Pat. No. 6,024,976 describes polymer blends that are useful in accordance with the transdermal systems described herein. The entire contents of U.S. Pat. No. 6,024,976 is incorporated herein by reference.

As used herein, the term "pressure-sensitive adhesive" refers to a viscoelastic material which adheres instantaneously to most substrates with the application of very slight pressure and remains permanently tacky. A polymer is a pressure-sensitive adhesive within the meaning of the term as used herein if it has the properties of a pressure-sensitive adhesive per se or functions as a pressure-sensitive adhesive by admixture with tackifiers, plasticizers or other additives.

The term pressure-sensitive adhesive also includes mixtures of different polymers and mixtures of polymers, such as polyisobutylenes (PIB), of different molecular weights, wherein each resultant mixture is a pressure-sensitive adhesive. In the last case, the polymers of lower molecular weight in the mixture are not considered to be "tackifiers," said term being reserved for additives which differ other than in molecular weight from the polymers to which they are added.

In some embodiments, the polymer matrix is a pressure-sensitive adhesive at room temperature and has other desirable characteristics for adhesives used in the transdermal drug delivery art. Such characteristics include good adherence to skin, ability to be peeled or otherwise removed without substantial trauma to the skin, retention of tack with aging, etc. In some embodiments, the polymer matrix has a glass transition temperature ($T_g$), measured using a differential scanning calorimeter, of between about −70° C. and 0° C.

As used herein, the term "rubber-based pressure-sensitive adhesive" refers to a viscoelastic material which has the properties of a pressure-sensitive adhesive and which contains at least one natural or synthetic elastomeric polymer.

In some embodiments, the transdermal drug delivery system includes one or more additional layers, such as one or more additional polymer matrix layers, or one or more adhesive layers that adhere the transdermal drug delivery system to the user's skin. In other embodiments, the transdermal drug delivery system is monolithic, meaning that it comprises a single polymer matrix layer comprising a pressure-sensitive adhesive or bioadhesive with drug dissolved or dispersed therein, and no rate-controlling membrane.

The transdermal drug delivery system also may include a drug impermeable backing layer or film. In some embodiments, the backing layer is adjacent one face of the polymer matrix layer. When present, the backing layer protects the polymer matrix layer (and any other layers present) from the environment and prevents loss of the drug and/or release of other components to the environment during use. Materials suitable for use as backing layers are well-known known in the art and can comprise films of polyester, polyethylene, vinyl acetate resins, ethylene/vinyl acetate copolymers, polyvinyl chloride, polyurethane, and the like, metal foils, nonwoven fabric, cloth and commercially available laminates. A typical backing material has a thickness in the range of 2 to 1000 micrometers. For example, 3M's Scotch Pak™ 1012 or 9732 backing material (a polyester film with an ethylene vinyl acetate copolymer heat seal layer) is useful in the transdermal drug delivery systems described herein.

The transdermal drug delivery system also may include a release liner, typically located adjacent the opposite face of the system as compared to the backing layer. When present, the release liner is removed from the system prior to use to expose the polymer matrix layer and/or an adhesive layer prior to topical application. Materials suitable for use as release liners are well-known known in the art and include the commercially available products of Dow Corning Corporation designated Bio-Release® liner and Syl-off® 7610 (both silicone-based) and 3M's 1020, 1022, 9744, 9748 and 9749 Scotchpak™ (fluoropolymer coated polyester films).

The transdermal drug delivery system may be packaged or provided in a package, such as a pouchstock material used in the prior art for transdermal drug delivery systems in general or for transdermal testosterone drug delivery systems in particular. For example, DuPont's Surlyn® can be used in a pouchstock material.

A used herein, a "monolithic" transdermal drug delivery system may include a backing layer and/or release liner, and may be provided in a package.

In accordance with some embodiments, the transdermal dug delivery system comprises a drug-containing polymer matrix layer that comprises a pressure-sensitive adhesive blend comprising an acrylic polymer, a silicone polymer, and a soluble PVP.

Acrylic Polymers

The term "acrylic polymer" is used here as in the art interchangeably with "polyacrylate," "polyacrylic polymer," and "acrylic adhesive." The acrylic-based polymers can be any of the homopolymers, copolymers, terpolymers, and the like of various acrylic acids or esters. In some embodiments, the acrylic-based polymers are adhesive polymers. In other embodiments, the acrylic-based polymers function as an adhesive by the addition of tackifiers, plasticizers, crosslinking agents or other additives.

The acrylic polymer can include copolymers, terpolymers and multipolymers. For example, the acrylic polymer can be any of the homopolymers, copolymers, terpolymers, and the like of various acrylic acids. In some embodiments, the acrylic polymer constitutes from about 2% to about 95% by weight of the polymer content of the polymer matrix, including about 3% to about 90% and about 5% to about 85%, such as 2% to 95%, 3% to 90% and 5% to 85%. In some embodiments, the amount and type of acrylic polymer is dependent on the type and amount of testosterone used.

Acrylic polymers useful in practicing the invention include polymers of one or more monomers of acrylic acids and other copolymerizable monomers. The acrylic polymers also include copolymers of alkyl acrylates and/or methacrylates and/or copolymerizable secondary monomers or monomers with functional groups. Combinations of acrylic-based polymers based on their functional groups is also contemplated. Acrylic-based polymers having functional groups include copolymers and terpolymers which contain, in addition to nonfunctional monomer units, further monomer units having free functional groups. The monomers can be monofunctional or polyfunctional. By varying the amount of each type of monomer added, the cohesive properties of the resulting acrylic polymer can be changed as is known in the art. In some embodiments, the acrylic polymer is composed of at least 50% by weight of an acrylate or alkyl acrylate monomer, from 0 to 20% of a functional monomer copolymerizable with the acrylate, and from 0 to 40% of other monomers.

Acrylate monomers which can be used include acrylic acid and methacrylic acid and alkyl acrylic or methacrylic esters such as methyl acrylate, ethyl acrylate, propyl acrylate, amyl acrylate, butyl acrylate, butyl methacrylate, hexyl acrylate, methyl methacrylate, hexyl methacrylate, heptyl acrylate, octyl acrylate, nonyl acrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, glycidyl acrylate, and corresponding methacrylic esters.

Non-functional acrylic-based polymers can include any acrylic based polymer having no or substantially no free functional groups.

Functional monomers, copolymerizable with the above alkyl acrylates or methacrylates, which can be used include acrylic acid, methacrylic acid, maleic acid, maleic anhydride, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate and methoxyethyl methacrylate.

As used herein, "functional monomers or groups," are monomer units typically in acrylic-based polymers which have reactive chemical groups which modify the acrylic-based polymers directly or which provide sites for further reactions. Examples of functional groups include carboxyl, epoxy, hydroxyl, sulfoxyl, and amino groups. Acrylic-based polymers having functional groups contain, in addition to the nonfunctional monomer units described above, further monomer units having free functional groups. The monomers can be monofunctional or polyfunctional. These functional groups include carboxyl groups, hydroxy groups, amino groups, amido groups, epoxy groups, etc. Typical carboxyl functional monomers include acrylic acid, methacrylic acid, itaconic acid, maleic acid, and crotonic acid. Typical hydroxy functional monomers include 2-hydroxyethyl methacrylate, 2-hydroxyethyl acrylate, hydroxymethyl acrylate, hydroxymethyl methacrylate, hydroxyethyl acrylate, hydroxyethyl methacrylate, hydroxypropyl acrylate, hydroxypropyl methacrylate, hydroxybutyl acrylate, hydroxybutyl methacrylate, hydroxyamyl acrylate, hydroxyamyl methacrylate, hydroxyhexyl acrylate, hydroxyhexyl methacrylate. As noted above, in some embodiments, the acrylic polymer does not include such functional groups.

Further details and examples of acrylic adhesives which are suitable in the practice of the invention are described in Satas, "Acrylic Adhesives," Handbook of Pressure-Sensitive Adhesive Technology, 2nd ed., pp. 396-456 (D. Satas, ed.), Van Nostrand Reinhold, New York (1989); "Acrylic and Methacrylic Ester Polymers," *Polymer Science and Engineering*, Vol. 1, 2nd ed., pp 234-268, John Wiley & Sons, (1984); U.S. Pat. No. 4,390,520; and U.S. Pat. No. 4,994,267, all of which are expressly incorporated by reference in their entireties.

Suitable acrylic polymers also include pressure-sensitive adhesives which are commercially available, such as the acrylic-based adhesives sold under the trademarks DURO-TAK® by National Starch and Chemical Corporation, Bridgewater, N.J. (such as DURO-TAK® 87-2287, -4098, -2852, -2196, -2296, -2194, -2516, -2070, -2353, -2154, -2510, -9085, -9088 and 73-9301). Other suitable acrylic adhesives include those sold under the trademark EUDRAGIT® by Roehm Pharma GmbH, Darmstadt, Germany, those sold by Cytec Surface Specialties, St. Louis, Mo., under the trademarks GELVA® Multipolymer Solution (such as GELVA® 2480, 788, 737, 263, 1430, 1753, 1151, 2450, 2495, 3067, 3071, 3087 and 3235). For example, hydroxy functional adhesives with a reactive functional OH group in the polymeric chain, can be used. Non-limiting commercial examples of this type of adhesives include both GELVA® 737, 788, and 1151, and DURO-TAK® 87-2287, -4287, -2510 and -2516.

Silicon Polymers

The term "silicone-based" polymer is used interchangeably with the terms silicon polymers, siloxane, polysiloxane, and silicones as used herein and as known in the art. A suitable silicone-based polymer may also be a pressure-sensitive adhesive. Thus, in some embodiments, the silicone-based polymer is an adhesive polymer. In other embodiments, the silicone-based polymer functions as an adhesive by the addition of tackifiers, plasticizers, crosslinking agents, or other additives.

Suitable polysiloxanes include silicone pressure-sensitive adhesives which are based on two major components: (i) a polymer or gum and (ii) a tackifying resin. A polysiloxane adhesive can be prepared by cross-linking a gum, typically a high molecular weight polydiorganosiloxane, with a resin, to produce a three-dimensional silicate structure, via a condensation reaction in an appropriate organic, volatile solvent, such as ethyl acetate or heptane. The ratio of resin to polymer can be adjusted in order to modify the physical properties of polysiloxane adhesives. Sobieski, et al., "Silicone Pressure Sensitive Adhesives," Handbook of Pressure-Sensitive Adhesive Technology, 2nd ed., pp. 508-517 (D. Satas, ed.), Van Nostrand Reinhold, New York (1989).

Exemplary silicone-based polymers are adhesives (e.g., capable of sticking to the site of topical application), including pressure-sensitive adhesives. Illustrative examples of silicone-based polymers having reduced silanol concentrations include silicone-based adhesives (and capped polysiloxane adhesives) such as those described in U.S. Pat. No. Re. 35,474 and U.S. Pat. No. 6,337,086, which are incorporated herein by reference in their entireties, and which are commercially available from Dow Corning Corporation (Dow Corning Corporation, Medical Products, Midland, Mich.) as BIO-PSA® 7-4100, -4200 and -4300 product series, and non-sensitizing, pressure-sensitive adhesives produced with compatible organic volatile solvents (such as ethyl acetate or heptane) and available commercially under their BIO-PSA® 7-4400 series, -4500 series, such as -4502, and -4600 series.

Further details and examples of silicone pressure-sensitive adhesives which are useful in the polymer matrices and compositions and methods described herein are mentioned in the following U.S. Pat. Nos. 4,591,622; 4,584,355; 4,585,836; and 4,655,767, which are all expressly incorporated by reference herein in their entireties. It should also be understood that silicone fluids are also contemplated for use in the polymer matrices and methods described herein.

In some embodiments, the polysiloxane constitutes from about 9% to about 97% of the polymer content of the polymer matrix, including about 8% to about 97% and about 14% to about 94%, such as 9% to 97%, 8% to 97%, and 14% to 94%.

Soluble PVP

In some embodiments, the polymer matrix includes soluble PVP. Soluble PVP has been found to be highly effective in preventing crystallization of drugs, such as testosterone, in adhesive-type transdermal drug delivery system. Soluble PVP also may modulate the transdermal permeation rate of the drug.

The term "PVP or "polyvinylpyrrolidone" refers to a polymer, either a homopolymer or copolymer, containing N-vinylpyrrolidone as the monomeric unit. Typical PVP polymers are homopolymeric PVPs and the copolymer vinyl acetate vinylpyrrolidone. The homopolymeric PVPs are known to the pharmaceutical industry under a variety of designations including Povidone, Polyvidone, Polyvidonum, Polyvidonum soluble, and Poly(1-vinyl-2-pyrrolidone). The copolymer vinyl acetate vinylpyrrolidone is known to the pharmaceutical industry as Copolyvidon, Copolyvidone, and Copolyvidonum. The term "soluble" when used with reference to PVP means that the polymer is soluble in water and generally is not substantially cross-linked, and has a molecular weight of less than about 2,000,000. See, generally, Buhler, KOLLIDON®: POLYVINYLPRYRROLIDONE FOR THE PHARMACEUTICAL INDUSTRY, BASF Aktiengesellschaft (1992).

The amount and type of soluble PVP used may depend on the quantity and type of testosterone present, as well as the type of adhesive, but can be readily determined through routine experimentation. Typically, the PVP is present in an amount from about 1% to about 20% by weight, preferably from about 5% to about 15% by weight, based on the total weight of the polymer matrix. However, the amount of PVP can be higher than 20% for example, up to 40%, depending on the particular drug used and on the desired properties of the blend. The soluble PVP may have a molecular weight of about 2,000 to 1,100,000, including 5,000 to 100,000, and 7,000 to 54,000. In some embodiments, the soluble PVP has a molecular weight of from about 17,000 to about 90,000, such as from about 17,000 to about 60,000, including from 17,000 to 90,000 and from 17,000 to 60,000.

In some embodiments, the polymer matrix comprises a soluble PVP with a rubber-based pressure-sensitive adhesive and a polyacrylate polymer, such as a blend of an acrylic polymer, a polysiloxane and a soluble PVP. In some embodiments, the blend is chosen to affect the rate of drug delivery. More specifically, a plurality of polymers including a soluble polyvinylpyrrolidone, which may have different solubility parameters for the drug and which may be immiscible with each other, may be selected to adjust the solubility of the drug in the polymer matrix, thereby controlling the maximum concentration of the drug in the system, and modulating drug delivery through the dermis.

The amount of acrylic-based polymer and silicone-based polymer can be adjusted so as to modify the saturation concentration of the drug in the polymer matrix in order to affect the rate of delivery of the drug from the system and through the skin. In some embodiments, the acrylic-based polymer and silicone-based polymer are used in a weight ratio of from about 2:98 to about 96:4, including about 2:98 to about 90:10 and 2:98 to about 86:14, such as 2:98 to 96:4, 2:98 to 90:10 and 2:98 to 86:14.

The concentration by weight of the testosterone in the transdermal drug delivery system is typically about 0.1 to about 50%, including about 0.1 to about 40% and about 0.3 to about 30%, such as 0.1 to 50%, 0.1 to 40% and 0.3 to 30%, all based on the total weight of the polymer matrix. In some embodiments, the testosterone is testosterone, and is present at an amount of from about 0.1 to 10%, including from about 0.1 to about 5%, such as from 0.1 to 10% and 0.1 to 5%, all based on the total dry weight of the polymer matrix. Irrespective of whether there is high-loading or low-loading of the testosterone into the transdermal drug delivery system, the pressure-sensitive adhesive composition can be formulated to maintain acceptable shear, tack, and peel adhesive properties.

Stabilizers

In some embodiments, the polymer matrix comprises a stabilizer that stabilizes the testosterone. For example, testosterone can be formulated with an antioxidant such as butylhydroxytoluene (BHT), butylhydroxyanisole (BHA), ascorbyl palmitate, alpha-tocopherol and its esters, citric acid and propyl gallate, and mixtures thereof. In some embodiments, a stabilizer may be used in an amount of about 0.001 to about 0.1% by weight, including about 0.01% by weight, such as 0.01% by weight, based on the dry weight of the polymer matrix.

Other Components

In one embodiment, the polymer matrix comprises a penetration enhancer. A "penetration enhancer" is an agent known to accelerate the delivery of the drug through the skin. These agents also have been referred to as accelerants, adjuvants, and sorption promoters, and are collectively referred to herein as "enhancers." This class of agents includes those with diverse mechanisms of action, including those which have the function of improving percutaneous absorption, for example, by changing the ability of the stratum corneum to retain moisture, softening the skin, improving the skin's permeability, acting as penetration assistants or hair-follicle openers or changing the state of the skin including the boundary layer.

Illustrative penetration enhancers include but are not limited to polyhydric alcohols such as dipropylene glycol, propylene glycol, and polyethylene glycol; oils such as olive oil, squalene, and lanolin; fatty ethers such as cetyl ether and oleyl ether; fatty acid esters such as isopropyl myristate; urea and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide, and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered. Other agents include oleic and linoleic acids, ascorbic acid, panthenol, butylated hydroxytoluene, tocopherol, tocopheryl acetate, tocopheryl linoleate, propyl oleate, and isopropyl palmitate.

In one embodiment, the penetration enhancer is oleyl alcohol. In another embodiment, the penetration enhancer is a glycol, such as dipropylene glycol, propylene glycol, butylene glycol or polyethylene glycol. In other embodiments, the penetration enhancer comprises a mixture of at least two penetration enhancers. For example, a penetration enhancer may comprise oleyl alcohol and one or more polyhydric alcohols, such as glycerine, dipropylene glycol, butylene glycol, propylene glycol. For instance, the penetration enhancer may include oleyl alcohol and dipropylene glycol.

In some embodiments, a penetration enhancer is used in an amount up to about 30% by dry weight of the polymer matrix, including up to 30% by weight, up to about 20% by weight, including 20% by weight, or up to about 10% by weight, up to 10% by weight, or up to 5% by weight, including up to 5% by weight, based on the dry weight of the polymer matrix. In some embodiments, a penetration enhancer is used in an amount of from about 5% to about 15%, such as from 5% to 15%. In specific embodiments, the penetration enhancer comprises a mixture of oleyl alcohol and dipropylene glycol which together amount to about 14% by weight of the polymer matrix. The polymer matrix may further comprise various thickeners, fillers, and other additives or components known for use in transdermal drug delivery systems.

The amount of testosterone to be incorporated in the polymer matrix varies depending on the particular drug, the desired therapeutic effect, and the time span for which the system is to provide therapy. For most drugs, the passage of the drugs through the skin will be the rate-limiting step in delivery. A minimum amount of drug in the system is selected based on the amount of drug which passes through the skin in the time span for which the system is to provide therapy. In some embodiments, a system for the transdermal delivery of testosterone is used over a period of about 1 day, about 3 days, about 7 days, or longer. Thus, in one embodiment, the systems comprise an amount of drug (e.g., testosterone) sufficient to deliver therapeutically effective amounts of drug over a period of from 1 day to 3 days, 7 days, or longer, including for 1 day, for 2 days, for 3 days, for 4 days, for 5 days, for 6 days, for 7 days, or for longer.

In some embodiments, a therapeutically effective amount of testosterone delivered by the composition is from about 100 to about 500 μg/day, including 100-500 μg/day and 100-450 μg/day, and further including at least about 300 μg/day, including 300 μg/day. Thus, in some embodiments, the transdermal drug delivery system comprises an amount of testosterone effective to achieve a delivery of from about 100 to about 500 μg/day, including 100-500 μg/day or 100-450 μg/day, or at least about 300 μg/day, including 300 μg/day. As noted above, in some embodiments, these rates are achieved over a duration of application of at least about 1 day, including at least about 3 days and at least about 7 days, such as at least 1 day, at least 2 days, at least 3 days, at least 4 days, at least 5 days, at least 6 days, and at least 7 days.

In some embodiments, the transdermal drug delivery system comprises a smaller amount of testosterone than an Intrinsa® product, but achieves comparable drug delivery. For example, in some embodiments a transdermal drug delivery system according to the invention may contain about 4 mg, including 3.94 mg, testosterone in a 14 cm$^2$ device, and achieve drug delivery comparable to an Intrinsa® product that contains about 8 mg, including 8.4 mg, testosterone in a 28 cm$^2$ device.

In some embodiments, the system comprises a polymer matrix comprising an amount of acrylic-based polymer of about 1 to about 70% by weight, including about 2 to about 25% by weight, based on the dry weight of the polymer matrix, such as 2-25% by weight acrylic-based polymer.

In some embodiments, the system comprises a polymer matrix comprising an amount of silicone polymer of about 5 to about 70% by weight, including about 45 to about 70% by weight, based on the dry weight of the polymer matrix, such as 45-70% by weight silicone polymer.

In some embodiments, the system comprises a polymer matrix comprising an amount of soluble PVP of about 1 to about 30% by weight, including about 2 to about 25% by weight, based on the dry weight of the polymer matrix, such as 2-25% by weight soluble PVP.

In some embodiments, the system comprises a polymer matrix comprising an amount of oleyl alcohol of about 1 to about 10% by weight, including about 4 to about 8% by weight, based on the dry weight of the polymer matrix, such as 4-8% by weight oleyl alcohol.

In some embodiments, the system comprises a polymer matrix comprising an amount of dipropylene glycol of about 1 to about 10% by weight, including about 5 to about 10% by weight, based on the dry weight of the polymer matrix, such as 5-10% by weight dipropylene glycol.

In some embodiments, the system comprises a polymer matrix comprising an amount of an antioxidant, such as butyl-hydroxytoluene (BHT), of about 0.001 to about 0.1% by weight, including about 0.01% by weight, based on the dry weight of the polymer matrix, such as 0.01% by weight butyl-hydroxytoluene (BHT).

In some embodiments, the polymer matrix comprises about 2-25% by weight acrylic adhesive, about 45-70% by weight silicone adhesive, about 2-25% by weight soluble PVP, about 0-15% penetration enhancer, and about 0.1-10% by weight testosterone, and, optionally, about 0.001 to about 0.1% by weight butylhydroxytoluene (BHT), all based on the dry weight of the polymer matrix. In specific embodiments, the polymer matrix comprises about 20% by weight acrylic adhesive, about 59% by weight silicone adhesive, about 12% by weight soluble PVP, about 6% by weight oleyl alcohol, about 2-3% by weight testosterone and, optionally, about 0.01% by weight butylhydroxytoluene (BHT).

In some embodiments, the acrylic adhesive and silicone adhesive are present in a ratio of from about 1:2 up to less than about 1:7, such as up to about 1:6, based on the weight of the acrylic and silicone adhesives. For example, in some embodiments, the acrylic adhesive and silicone adhesive are present in a ratio of about 1:2, 1:3, 1:4, 1:5 or 1:6, based on the weight of the acrylic and silicone adhesives. In specific embodiments, the acrylic adhesive and silicone adhesive are present in a ratio of 1:2.8, based on the weight of the acrylic and silicone adhesives.

As noted above, in embodiments where the polymer matrix comprises a pressure-sensitive adhesive or bioadhesive, the polymer matrix can serve as an adhesive portion of the system (e.g., a reservoir device), or can serve as one or more layers of a multi-layer system. Alternatively, a polymer matrix comprising a pressure-sensitive adhesive or bioadhesive with drug dissolved or dispersed therein can constitute a monolithic device. In embodiments where the polymer matrix does not comprise an adhesive, but instead, for example, comprises a polymeric drug reservoir, it can be used in combination with one or more adhesive layers, or with a surrounding adhesive portion, as is well known to those skilled in the art.

In some embodiments, the system consists essentially of the polymer matrix layer. By "consists essentially of the polymer matrix layer" means that the system does not contain any other layers that affect drug delivery, such as an additional rate-controlling polymer layer, rate-controlling membrane, or drug reservoir layer. It will be understood, however, that the system that consists essentially of the polymer matrix layer may comprise a backing layer and/or release liner.

As discussed above, in some embodiments, the systems have a greater flux than other known testosterone devices for use by females (such as Intrinsa®, manufactured by Watson Pharmaceuticals Inc.), and, therefore, exhibit increased drug delivery per unit area of the active surface area. For example, in some embodiments, the systems exhibit a flux greater than the about 0.45 µg/cm²/hour exhibited by the Intrinsa® product, such as a flux that is about double, such as a flux of about 0.89 µg/cm²/hour. In some embodiments, the systems described herein achieve a flux that is at least about 0.7 µg/cm²/hour, including at least 0.7 µg/cm²/hour, including at least about 0.89 µg/cm²/hour and at least 0.89 µg/cm²/hour, or at least about 1.0 µg/cm²/hour, including at least 1.0 µg/cm²/hour, over a period of time of at least about 1 day, including at least about 3 days and at least about 7 days, such as at least 1 day, at least 2 days, at least 3 days, at least 4 days, at least 5 days, at least 6 days, and at least 7 days.

In some embodiments, the systems have a different coat weight than other known testosterone devices. In some embodiments, the polymer matrix has a coat weight of greater than about 10 mg/cm². In some embodiments, the polymer matrix has a coat weight selected from the group consisting of about 12.0, about 12.5, about 13.0 and about 15 mg/cm².

In some embodiments, the systems have an amount of testosterone per unit area of the active surface area that is less than the 0.3 mg/cm² testosterone of the Intrinsa® product, such as an amount of testosterone of about 0.28 mg/cm².

The system may be of any shape or size suitable for transdermal application. In some embodiments, the systems are smaller than the Intrinsa® product, but achieve comparable daily dosages. For example, the systems may have an active surface area of 50% of the active surface area of an Intrinsa product, such as about 50% of 28 cm², and deliver a daily dosage of testosterone comparable to that of the Intrinsa® product, such as an amount of testosterone of at least about 300 µg/day. In one embodiment, the system has an active surface area of about 14 cm² and delivers a daily dosage of testosterone comparable to that of the 28 cm² Intrinsa® product, e.g., about 300 µg/day.

The polymer matrices described herein may be prepared by methods known in the art. The polymer matrices can be formed into systems by methods known in the art. For example, the polymer matrix material can be applied to a backing layer and release liner by methods known in the art, and formed into sizes and shapes suitable for use.

For example, after the polymer matrix is formed, it may be brought into contact with a support layer, such a releaser liner layer or backing layer, in any manner known to those of skill in the art. Such techniques include calendar coating, hot melt coating, solution coating, etc.

For example, a polymer matrix can be prepared by blending the components of the polymer matrix, applying the matrix material to a support layer such as a backing layer or release liner, and removing any remaining solvents. The testosterone can be added at any stage. In one embodiment, all polymer matrix components, including testosterone, are blended together. In another embodiment, the polymer matrix components other than testosterone are blended together, and then the testosterone is dissolved or dispersed therein. The order of steps, amount of ingredients, and the amount and time of agitation or mixing can be determined and optimized by the skilled practitioner. An exemplary general method is as follows:

Appropriate amounts of soluble PVP, solvent(s), enhancer(s), and organic solvent(s) (for example toluene, or ethyl acetate an/or isopropyl alcohol) are combined and thoroughly mixed together in a vessel.

Testosterone and any antioxidant being used (such as BHT) are added to the mixture and agitation is carried out until the drug is uniformly mixed in.

Appropriate amounts of polysiloxane and acrylic polymer are then added to the drug mixture, and thoroughly mixed.

The formulation is then transferred to a coating operation where it is coated onto a protective release liner at a controlled specified thickness. The coated product is then passed through an oven in order to drive off all volatile processing solvents.

The dried product on the release liner is then joined to the backing material and wound into rolls for storage.

Appropriate size and shape "systems" are die-cut from the roll material and then pouched.

Other manufacturing methods are known in the art that are suitable for making the systems described herein.

In some embodiments, there is provided a method of effecting transdermal drug delivery of testosterone, such as testosterone, by applying a system as described herein to the skin or mucosa of a subject in need thereof. In some embodiments, the system comprises testosterone, and the system is applied over a period of at least about 1 day, at least about 2 days, at least about 3 days, at least about 4 days, at least about 5 days, at least about 6 days, or at least about 7 days, such as for 1, 2, 3, 4, 5, 6 or 7 days. In some embodiments, the method is effective to achieve therapeutic levels of testosterone in the subject during the application period. As noted above, a typical testosterone dosage ranges from at least about 100 to about 500 μg/day, including 100-500 μg/day and 100-450 μg/day, including at least about 300 μg/day, including 300 μg/day.

In some embodiments, the systems described herein are designed for use by female patients, including female patients undergoing testosterone therapy for congestive heart failure. In other embodiments, the systems described herein are designed for use by female patients undergoing hormone replacement therapy or therapy to improve their libido. In some embodiments, the systems described herein may be designed are adapted for use by male patients.

The following specific examples are included as illustrative of the transdermal drug delivery systems and polymer matrices described herein. These example are in no way intended to limit the scope of the invention. Other aspects of the invention will be apparent to those skilled in the art to which the invention pertains.

Example 1

A polymer matrix with the following composition is prepared:

| Ingredient | % w/w in Finished Dry Product |
|---|---|
| Silicone polymer (BIO PSA 4502) | 59.74 |
| Acrylic polymer (Gelva 788) | 20.00 |
| PVP (Povidone 30) | 12.00 |
| Oleyl Alcohol | 6.00 |
| Butylated Hydroxytoluene | 0.01 |
| Testosterone USP, CIII | 2.25 |
| Total | 100.00 |

The polymer matrix is applied with a coat weight of 12.5 mg/cm$^2$ to a Scotch Pak™ 1022 release liner, and Scotch Pak™ 9732 (polyethylene) backing material is applied. Individual systems with an active surface area of 14 cm$^2$ are prepared. The systems are packaged in Surlyn® 0.0007 pouchstock material.

Human cadaver skin permeation studies are performed to quantitatively determine the effective permeation through the stratum corneum. The stratum corneum is obtained from split thickness, cryo-preserved cadaver skin by the heat separation technique. Samples of 5/16" diameter are cut from the laminate, in quadruplicate, and mounted onto ½" cut pieces of the stratum corneum. These samples are place on modified Franz diffusion cells. The receptor is filled with 7.5 mL of 0.9% NaCl and 0.01% NaN$_3$ in deionized water. The cells are maintained at a constant 32° C. and magnetically stirred at approximately 300 rpm. At specified time points, samples of the receptor phase are taken with complete replacement of the receptor phase. These samples are quantified by high-performance liquid chromatography (HPLC) utilizing Waters HPLC instrumentation. C-8 (15 cm×4.6 mm) 5 μm particle size columns (HYPERSIL made by MetaChem Technologies, Inc., Torrance, Calif.) are used at 50° C. (column temperature).

FIG. 1 illustrates the testosterone flux (μg/cm$^2$/hr) over time (0-96 hours) from a transdermal delivery system according to the invention (●, top line), as compared to Intrinsa® (♦, bottom line).

Figure 2:
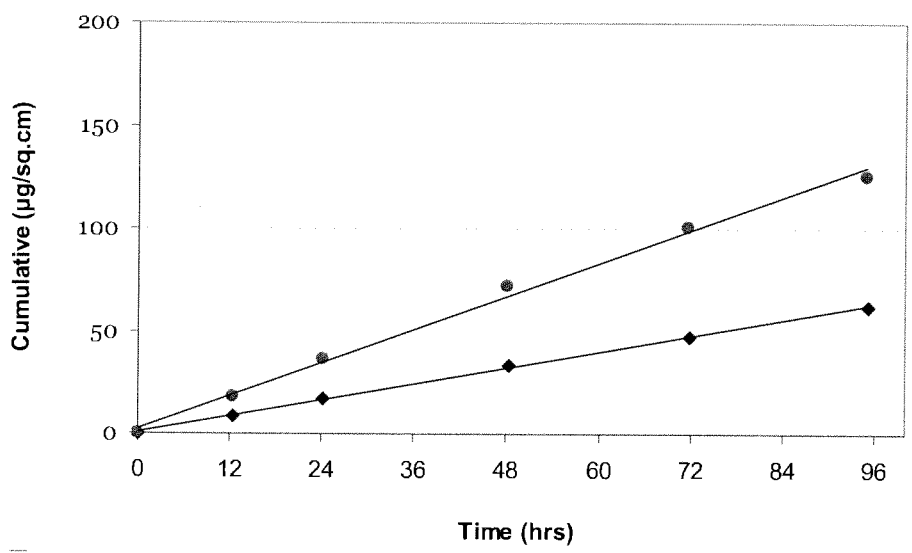
FIG. 2 illustrates the cumulative amount of drug delivered per unit area (µg/cm²) over time (0-96 hours) from a transdermal delivery system according to the invention (●), as compared to Intrinsa® (♦).

FIG. 2 illustrates the cumulative amount of drug delivered per unit area (μg/cm$^2$) over time (0-96 hours) from a transdermal delivery system according to the invention (●, top line), as compared to Intrinsa® (♦, bottom line).

The results show that the system according to the invention achieves a greater flux than the Intrinsa® product and is able to achieve therapeutic daily dosages (such as at least 300 μg/day over three to four days) despite its significantly smaller size.

What is claimed is:

1. A transdermal drug delivery system comprising a drug-containing layer defining an active surface area and comprising a polymer matrix comprising about 20% by weight acrylic adhesive, about 59% by weight silicone adhesive, about 12% by weight soluble polyvinylpyrrolidone (PVP), about 6% by weight oleyl alcohol, and about 2-3% by weight testosterone, all based on the total dry weight of the polymer matrix, wherein the system includes less than 0.3 mg/cm$^2$ testosterone, and achieves a testosterone flux that is at least 0.7 μg/cm$^2$/hour, based on the active surface area, wherein the polymer matrix comprises an amount of testosterone effective to deliver an amount of testosterone from about 100 to about 500 μg/day.

2. The transdermal drug delivery system of claim 1, wherein the system achieves a testosterone flux that is at least 0.89 μg/cm$^2$/hour, based on the active surface area.

3. The transdermal drug delivery system of claim 1, wherein the composition further comprises an antioxidant selected from the group consisting of butylhydroxytoluene (BHT), butylhydroxyanisole (BHA), ascorbyl palmitate, alpha-tocopherol and its esters, citric acid and propyl gallate, and mixtures thereof.

4. The transdermal drug delivery system of claim 3, wherein the antioxidant comprises BHT.

5. The transdermal drug delivery system of claim 1, wherein the polymer matrix comprises an amount of testosterone effective to deliver a therapeutically effective amount of testosterone over a period of time selected from the group consisting of at least 1 day, at least 2 days, at least 3 days, at least 4 days, at least 5 days, at least 6 days and at least 7 days.

6. The transdermal drug delivery system of claim 1, wherein the polymer matrix comprises an amount of testosterone effective to deliver an amount of testosterone of from about 100 to about 450 µg/day.

7. The transdermal drug delivery system of claim 1, wherein the polymer matrix comprises an amount of testosterone effective to deliver an amount of testosterone of from about 300 µg/day to about 500 µg/day.

8. The transdermal drug delivery system of claim 4, wherein the polymer matrix comprises about 0.01% by weight BHT, based on the total dry weight of the polymer matrix.

9. The transdermal drug delivery system of claim 1, wherein the polymer matrix has a coat weight of greater than about 10 mg/cm$^2$.

10. The transdermal drug delivery system of claim 1, wherein the polymer matrix has a coat weight of about 12.5 mg/cm$^2$.

11. A transdermal drug delivery system comprising a polymer matrix comprising about 20% by weight acrylic adhesive, about 59% by weight silicone adhesive, about 12% by weight soluble polyvinylpyrrolidone (PVP), about 6% by weight oleyl alcohol, and about 2-3% by weight testosterone, all based on the total dry weight of the polymer matrix, wherein the system has an active surface area of 14.0 cm$^2$ and is effective to deliver an amount of testosterone per day of from about 300 µg to about 500 µg.

\* \* \* \* \*